US010034793B2

(12) United States Patent
Leise, Jr.

(10) Patent No.: US 10,034,793 B2
(45) Date of Patent: Jul. 31, 2018

(54) COUPLING SYSTEMS INCLUDING INTERLOCKING MALE AND FEMALE MEMBERS

(71) Applicant: Sarasota Medical Products, Inc., Sarasota, FL (US)

(72) Inventor: Walter F. Leise, Jr., Sarasota, FL (US)

(73) Assignee: SARASOTA MEDICAL PRODUCTS, INC., Sarasota, FL (US)

( * ) Notice: Subject to any disclaimer, the term of this patent is extended or adjusted under 35 U.S.C. 154(b) by 446 days.

(21) Appl. No.: 14/739,846

(22) Filed: Jun. 15, 2015

(65) Prior Publication Data

US 2015/0359658 A1 Dec. 17, 2015

Related U.S. Application Data

(60) Provisional application No. 62/012,824, filed on Jun. 16, 2014.

(51) Int. Cl.
*A61F 5/448* (2006.01)
*A61F 5/44* (2006.01)
*B65D 43/02* (2006.01)

(52) U.S. Cl.
CPC .......... *A61F 5/448* (2013.01); *A61F 5/4404* (2013.01); *B65D 43/0204* (2013.01); *B65D 2543/005* (2013.01); *B65D 2543/00537* (2013.01); *Y10S 215/01* (2013.01)

(58) Field of Classification Search
CPC .......... A61F 5/448; A61F 5/4404; A61F 5/44; A61F 5/4407; A61F 5/4408
See application file for complete search history.

(56) References Cited

U.S. PATENT DOCUMENTS

| | | | | |
|---|---|---|---|---|
| 3,255,907 A | * | 6/1966 | Eddy | B65D 41/0428 215/329 |
| 3,473,685 A | * | 10/1969 | Karlan | B65D 41/525 215/253 |
| 3,759,415 A | * | 9/1973 | Cloyd | B65D 43/0212 220/324 |
| 4,232,672 A | * | 11/1980 | Steer | A61F 5/441 604/333 |
| 4,344,612 A | | 8/1982 | Leise et al. | |
| 4,347,943 A | * | 9/1982 | Hackwell | B65D 43/0212 215/320 |
| 4,426,014 A | * | 1/1984 | Coltman, Jr. | B65D 43/022 215/DIG. 1 |
| 4,682,707 A | * | 7/1987 | Wiles | B65D 43/0272 138/89 |
| 4,772,134 A | | 9/1988 | Jensen et al. | |
| 4,775,373 A | * | 10/1988 | Steer | A61F 5/443 604/338 |

(Continued)

FOREIGN PATENT DOCUMENTS

EP 1413268 B1 4/2009

*Primary Examiner* — Adam Marcetich
(74) *Attorney, Agent, or Firm* — Quarles and Brady LLP

(57) ABSTRACT

Coupling systems including interlocking male and female members are disclosed herein. An example apparatus includes a first coupling including a sidewall having an annular spring. The example apparatus also includes a second coupling to be coupled to the first coupling. The second coupling has an annular wall including a seal. The seal is to sealingly engage the annular spring when the second coupling is coupled to the first coupling.

20 Claims, 5 Drawing Sheets

(56) References Cited

U.S. PATENT DOCUMENTS

| | | | |
|---|---|---|---|
| 4,820,285 A | 4/1989 | Leise et al. | |
| 4,823,967 A * | 4/1989 | Thompson | B65D 41/0414 215/222 |
| 4,872,869 A | 10/1989 | Johns | |
| 4,892,530 A | 1/1990 | Steer | |
| 4,938,750 A | 7/1990 | Leise et al. | |
| 5,004,464 A | 4/1991 | Leise | |
| 5,074,852 A | 12/1991 | Castellana et al. | |
| 5,088,992 A | 2/1992 | Edwards et al. | |
| 5,139,492 A | 8/1992 | Leise et al. | |
| 5,167,651 A | 12/1992 | Leise et al. | |
| 5,185,008 A | 2/1993 | Lavender | |
| 5,195,996 A | 3/1993 | Edwards et al. | |
| 5,275,287 A * | 1/1994 | Thompson | B65D 41/0421 215/341 |
| 5,320,236 A * | 6/1994 | Gregory | B65D 41/0428 215/341 |
| 5,330,154 A | 7/1994 | Klinger et al. | |
| 5,330,455 A * | 7/1994 | McKay | A61F 5/448 604/332 |
| 5,401,264 A | 3/1995 | Leise | |
| 5,520,670 A | 5/1996 | Blum | |
| 5,540,342 A * | 7/1996 | Rathbun | B65D 43/0256 215/225 |
| 5,618,276 A | 4/1997 | Leise, Jr. et al. | |
| 5,693,035 A | 12/1997 | Leise, Jr. et al. | |
| 5,803,286 A * | 9/1998 | Pfefferkorn | B65D 51/1661 215/307 |
| 5,947,941 A | 9/1999 | Leise, Jr. et al. | |
| 5,954,215 A * | 9/1999 | Alter | B65D 41/185 215/318 |
| 6,093,276 A | 7/2000 | Leise, Jr. et al. | |
| 6,106,507 A | 8/2000 | Botten et al. | |
| 6,197,010 B1 | 3/2001 | Leise, Jr. et al. | |
| 6,537,261 B1 * | 3/2003 | Steer | A61F 5/448 604/342 |
| 6,569,134 B1 | 5/2003 | Leise, Jr. et al. | |
| 6,673,056 B2 | 1/2004 | Metz et al. | |
| 6,726,667 B2 | 4/2004 | Leise, Jr. et al. | |
| 6,740,067 B2 | 5/2004 | Leise, Jr. et al. | |
| 6,772,894 B1 * | 8/2004 | Druitt | B65D 41/0428 215/252 |
| 2003/0021919 A1 * | 1/2003 | Granger | B65D 41/0428 428/34.1 |
| 2003/0028160 A1 | 2/2003 | Leise, Jr. et al. | |
| 2003/0073965 A1 | 4/2003 | Leise, Jr. et al. | |
| 2003/0088219 A1 | 5/2003 | Metz et al. | |
| 2003/0155365 A1 * | 8/2003 | Llorente Lecue | B65D 43/021 220/802 |
| 2003/0171737 A1 | 9/2003 | Leise, Jr. et al. | |
| 2004/0106908 A1 | 6/2004 | Leise, Jr. et al. | |
| 2004/0256346 A1 * | 12/2004 | Becker | B65D 1/0246 215/44 |
| 2008/0105641 A1 * | 5/2008 | Dobbelstein | B65D 41/3438 215/253 |
| 2008/0110851 A1 * | 5/2008 | Fuchs | B65D 41/0421 215/344 |
| 2008/0230550 A1 * | 9/2008 | Burney | B65D 43/0212 220/792 |
| 2010/0213195 A1 * | 8/2010 | Baltz | B65D 25/32 220/309.1 |
| 2012/0022436 A1 | 1/2012 | Bradley et al. | |

\* cited by examiner

COUPLING SYSTEMS INCLUDING INTERLOCKING MALE AND FEMALE MEMBERS

CROSS REFERENCE TO RELATED APPLICATIONS

This application claims the benefit of U.S. Provisional Application No. 62/012,824, entitled "Coupling Systems Including Interlocking Male and Female Members" and filed on Jun. 16, 2014. U.S. Provisional Application No. 62/012,824 is incorporated by reference herein in its entirety.

REFERENCE REGARDING FEDERALLY SPONSORED RESEARCH AND DEVELOPMENT

Not applicable

SEQUENCE LISTING

Not applicable

BACKGROUND

Field of the Disclosure

The present disclosure is related to advanced wound care and ostomy medical devices to be attached to a human body, in which a male member is connected to the body and two separate components can be connected and disconnected multiple times.

Description of the Related Art

Known ostomy devices, such as those described below, typically include releasable inter-engaging parts in the form of coupling rings, which permit detachment of a collection pouch from an adhesive backed faceplate. The inter-engaging parts typically lack a secure connection. In addition, a body side of known ostomy devices generally cannot be cleaned by the user during replacement of the pouch.

For example, U.S. Pat. No. 5,947,941 discloses a two-piece ostomy device that has a modified rocking wedge for coupling rings having a low profile and reduced coupling force. This device maintains a gas tight seal though a wiper on a component attached to the body. In addition, this device maintains security components on a detachable pouch. During normal body movements, the body side component has reduced flexibility and less security. In this device's field of use, the bag side of this device is changed multiple times. During the replacement of the pouch, the body side of this device is retained and unable to be cleaned by the user. Similarly, other prior art devices such as described in U.S. Pat. Nos. 4,892,530, 4,872,869, 5,185,008, 5,195,996, 5,520,670, 5,947,941, 6,197,010 and U.S. Pub. No. 2012/0022436, exhibit such properties as well.

Therefore, there is a need to provide an ostomy device having inter-engaging coupling rings that are flexible, in relation to each other, but exhibit an uncoupling force that is substantially higher during normal body movements than known in the prior art. Providing a flexible interface will enhance the integrity of the seal, maintain a secure connection to prevent inadvertent disconnection, and provide for an overall more stable and durable device. In addition, there is a need to provide the user with a body side component that does not retain waste and increases hygiene. The present disclosure addresses these concerns and provides a solution.

SUMMARY

An example apparatus disclosed herein includes a male coupling to be secured to a patient. The male coupling includes a first sidewall having a first wall portion, a second wall portion, and a recess between the first wall portion and the second wall portion. The recess enables relative movement between the first wall portion and the second wall portion. The example apparatus also includes a female coupling to be coupled to a pouch. The female coupling includes a second sidewall and an interior wall spaced apart from the second sidewall. The interior wall has a flexible seal. The first sidewall of the male coupling is to be received between the second sidewall and the interior wall of the female coupling to form a seal between the second wall portion of the male coupling and the flexible seal of the female coupling.

Another example apparatus disclosed herein includes a first coupling including a sidewall having an annular spring. The example apparatus also includes a second coupling to be coupled to the first coupling. The second coupling has an annular wall including a seal. The seal is to sealingly engage the annular spring when the second coupling is coupled to the first coupling.

Another example apparatus disclosed herein includes a male coupling including a first sidewall having a generally V-shaped cross-sectional profile. The apparatus also includes a female coupling including a second sidewall having a generally U-shaped cross-sectional profile. The first sidewall is to interlock with the second sidewall.

BRIEF DESCRIPTION OF THE DRAWINGS

Other aspects and advantages of the apparatus, systems, and methods disclosed herein will become apparent upon consideration of the following detailed description, wherein similar structures have similar reference numerals

DETAILED DESCRIPTION

Coupling systems are disclosed herein. The coupling systems may be employed as a medical appliance that joins an ostomy bag or wound care manifold to a faceplate capable of adhesively securing to a patient's skin. In some embodiments, the coupling systems include coupling rings formed of flexible and resilient thermoplastic material. The coupling rings may include a female component having a gas and odor seal and a security tab. The coupling rings may also include a male component having an extended interior wall to increase patient hygiene and minimize fecal contamination. The male component may include a deflectable spring to maintain a firm seal, while retaining flexibility. The male component may include a security feature, and the security feature and the deflectable spring work in concert with the security tab of the female component to produce an audible click when the male and female components are joined. In some embodiments, the inter-engaging coupling rings are flexible in relation to each other and exhibit an uncoupling force that is substantially higher during normal body movements than traditional coupling systems for ostomy devices. The systems disclosed herein provide a flexible interface with enhanced seal integrity, maintain a secure connection to prevent inadvertent disconnection, and provide for a more stable and durable coupling system than traditional coupling systems for ostomy devices. In addition, the systems disclosed herein provide the user with a body side component that does not retain waste and, thus, increases hygiene.

Figure 1:
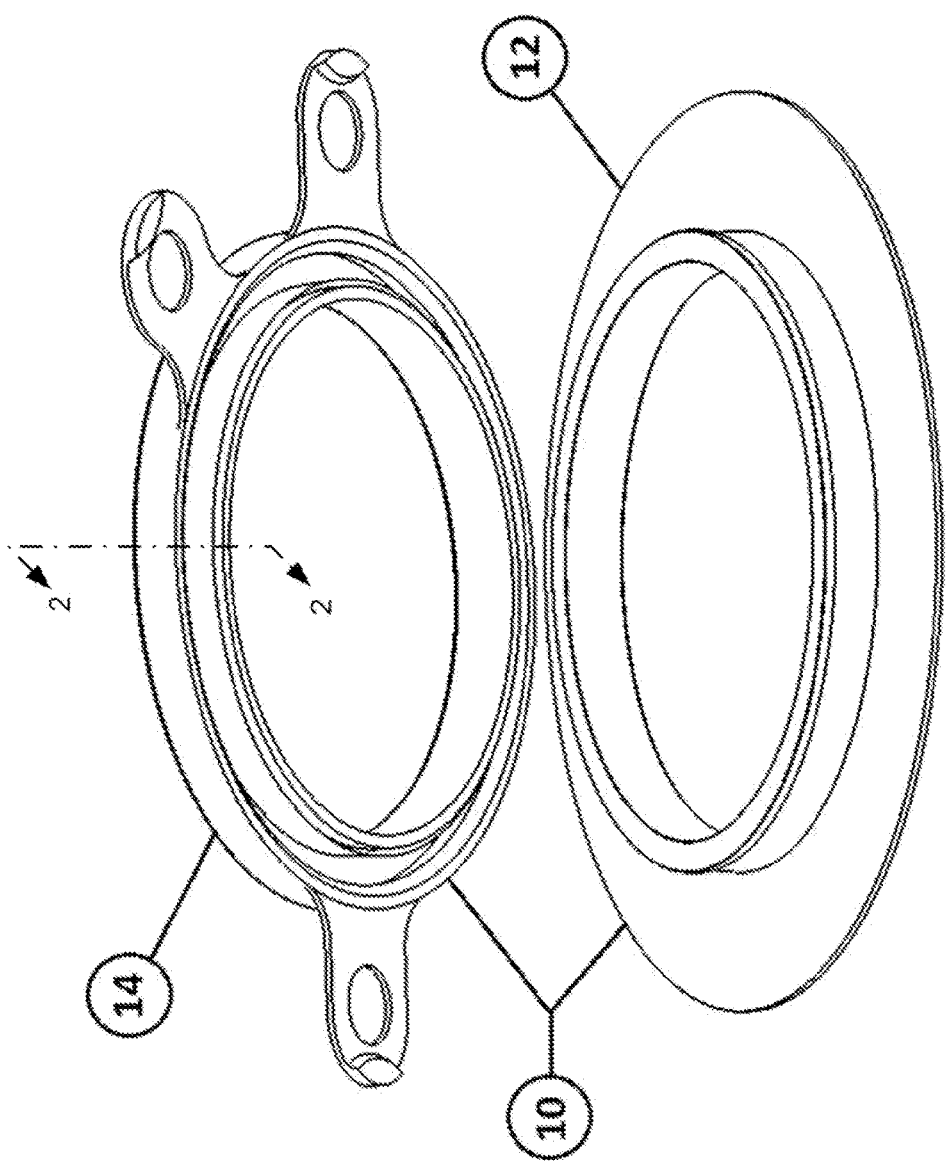
FIG. 1 is an isometric view of a coupling system having unjoined male and female security features.
Figure 2:
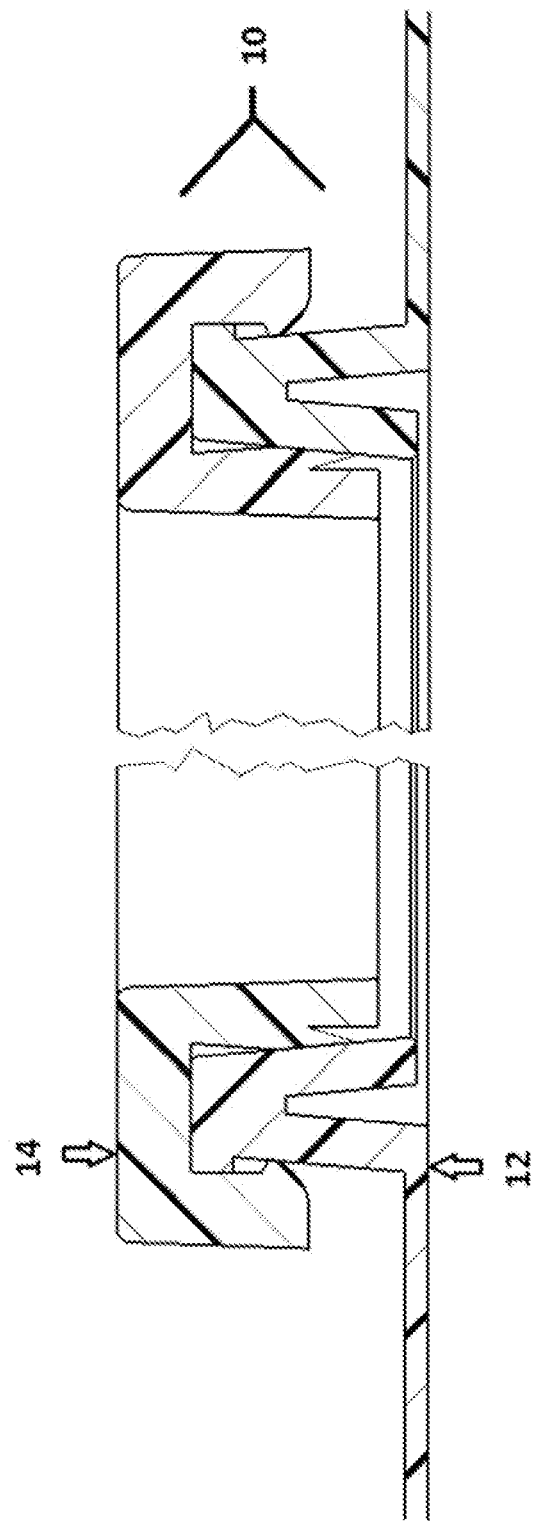
FIG. 2 is a sectional view of the security features of FIG. 1 shown in a conjoined state, taken along the line 2-2 thereof.

FIG. 1 depicts a coupling system 10 comprising a male member 12 and a female member 14 shown in an unjoined state. FIG. 2 depicts a cross section of the coupling system 10 in a conjoined manner. The coupling system 10 may be any suitable size.

Figure 3:
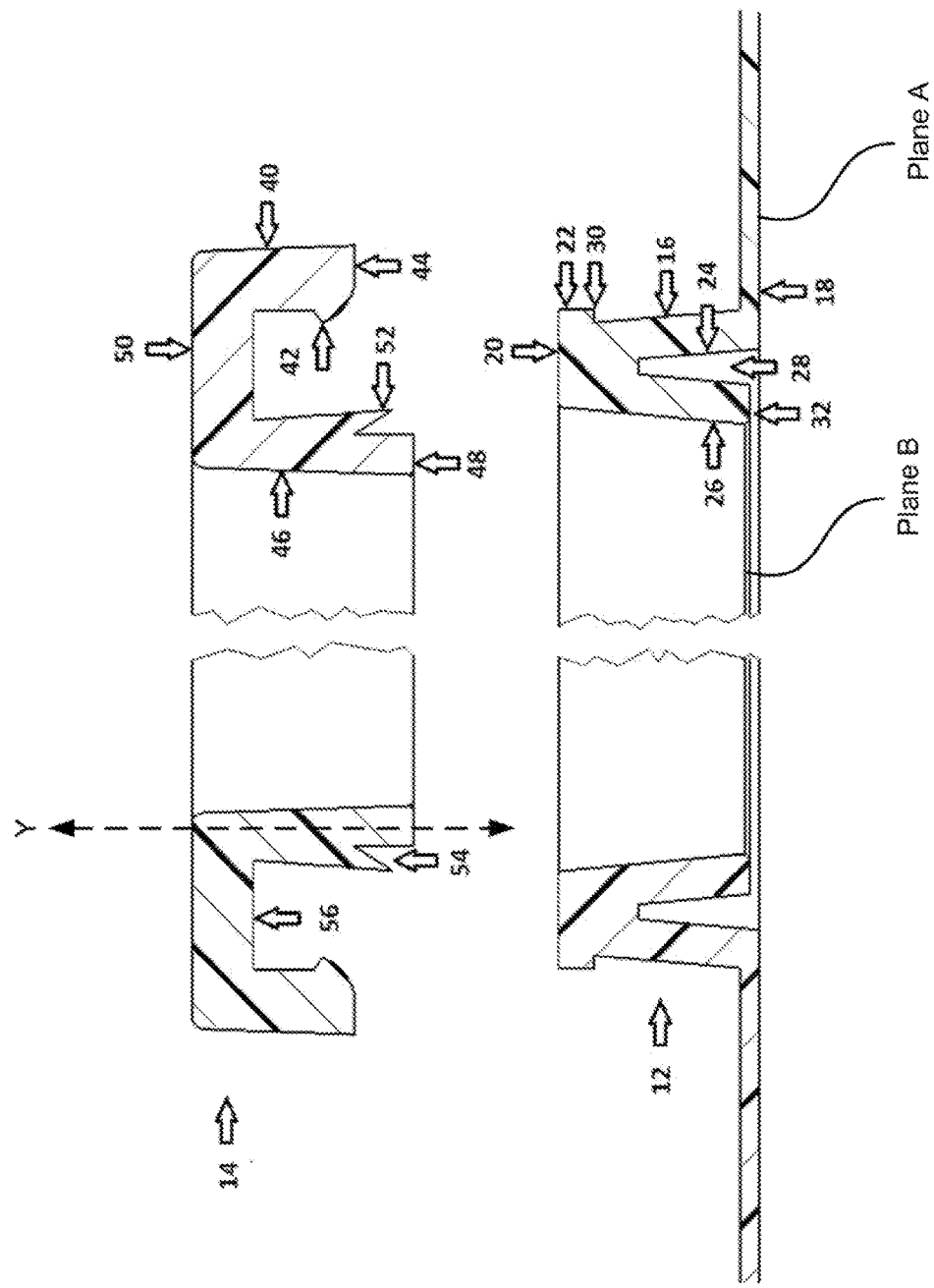
FIG. 3 is an exploded sectional view of the male and female security features of FIG. 2 shown in an unjoined state.
Figure 4:
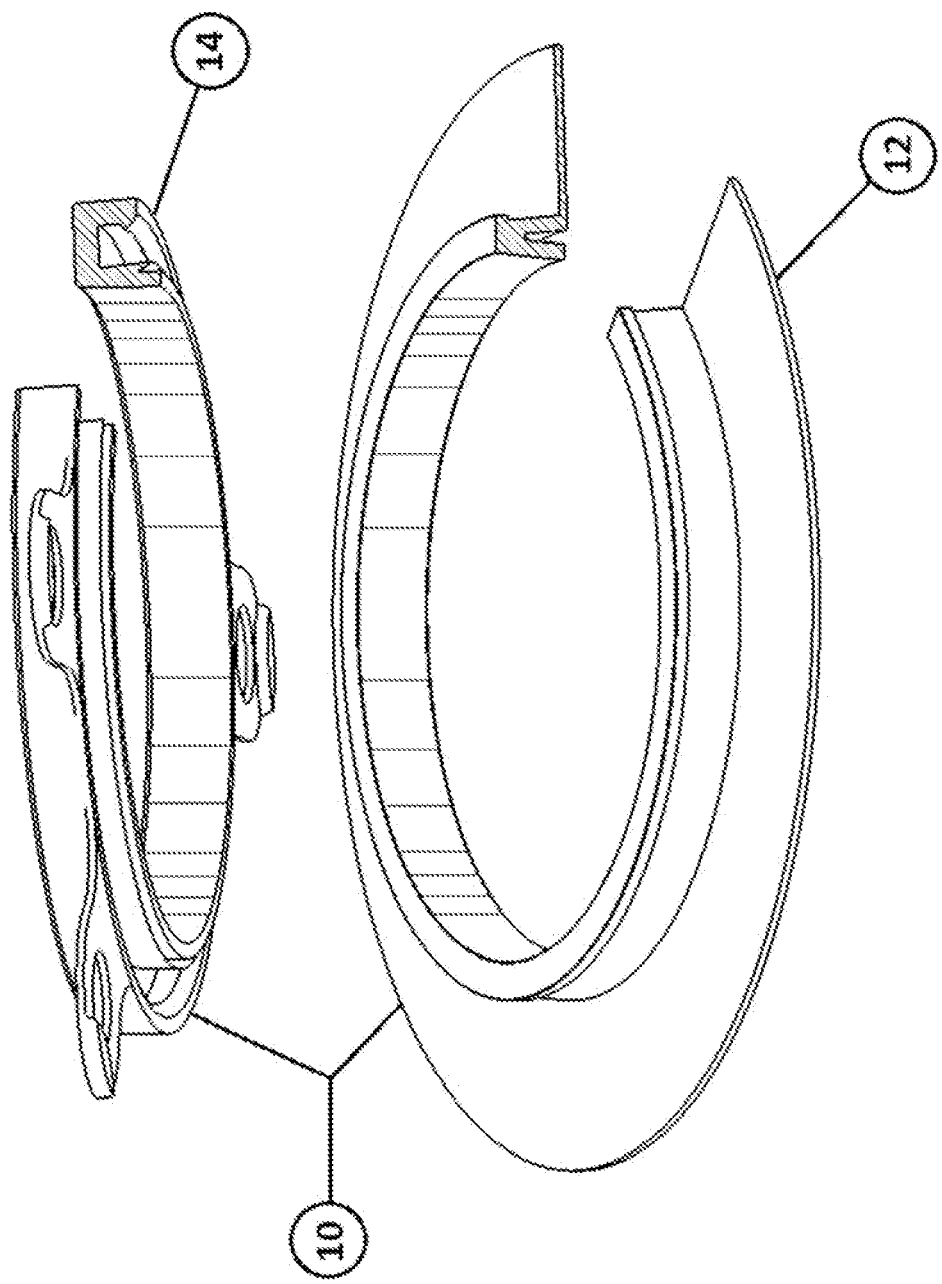
FIG. 4 is an isometric view of a coupling system having unjoined male and female security features with a section removed for purposes of clarity.

With reference now to FIG. 3, the female member 14 is positioned above the male member 12. The male member 12 includes an annular sidewall 16 with a lower end 18 and an upper end 20. A peripheral extension 22 extends outwardly from the upper end 20. The sidewall 16 generally includes a first or outer wall portion 24 and a second or inner wall portion 26, both of which are also generally annular in shape and depend from the upper end 20 of the sidewall 16. In the illustrated embodiment, the inner wall portion 26 is a depending flange. A recess 28 is formed between the outer and inner wall portions 24, 26 between the upper and lower ends 20, 18. In the present embodiment, the recess 28 extends upwardly from the lower end 18 to about a medial portion of the sidewall 16. The peripheral extension 22 extends from the upper end 20 to an inner bottom end 30.

In some embodiments, the male member's 12 recess 28 provides an uninterrupted annular recess that acts as a tensioned spring to maintain integrity but allow for flexibility during normal body movements. For example, the recess 28 may enable relative movement between the outer and inner wall portions 24, 26 during normal body movements. The outer wall portion 24 extends from the medial portion of the sidewall 16 to the lower end 18 thereof (see plane A) positioned adjacent a plane B defined by a bottom end 32 of the inner wall portion 26. In some embodiments, the distance between the lower end 18 and the bottom end 32 of the outer and inner wall portions 24, 26, respectively, is at least about 20 microns. In the instance where a non-uniform bottom end 32 is provided, the lowermost portions of the lower end 18 and the bottom end 32 are preferably at least 20 microns apart. The provision of the distance or gap allows for the insertion of convex discs. The above-noted dimensions are merely examples, and thus, other dimensions can be used without departing from the scope of this disclosure. In the illustrated embodiment, the male member 12 has no area within the inner wall portion 26 that can become contaminated with fecal matter.

With continued reference to FIG. 3, the female member 14 is shown to include an outer annular sidewall 40 with a protrusion 42 extending from a lower end 44 thereof. An interior annular sidewall 46 is provided interiorly of the outer annular wall 40 and extends between lower and upper ends 48, 50, respectively. The interior annular sidewall 46 includes a deflectable gas-odor seal 52, which provides a variable recess 54. For example, the seal 52 may deform when engaged with the inner wall portion 26. As a result, the seal 52 may move toward the interior annular sidewall 46, decreasing a width or span of the recess 54. An upper wall 56 extends between the outer and interior annular sidewalls 40, 46.

With reference now to FIGS. 1-4 the coupling of the system 10 will be described. As shown in FIG. 1, the male member 12 and the female member 14 are positioned proximate one another prior to engagement. Thereafter, as illustrated in FIG. 3, one or both of the members 12, 14 are pressed toward one another so that the upper end 20 of the male member 12 is positioned adjacent the lower end 48 of the interior annular sidewall 46 of the female member 14. As the user joins the two members 12, 14 together, several interactions occur simultaneously and/or in temporal proximity to one another. One such interaction is that the inner wall portion 26 of the male member 12 and the gas-odor seal 52 of the female member 14 mutually deflect toward the respective recesses 28, 54 in the members 12, 14, respectively. With reference to FIG. 2, as pressure is applied by the user to mate the two members 12, 14, the protrusion 42 of the female member 14 passes the peripheral extension 22 of the male member 12, and the protrusion 42 and the peripheral extension 22 cooperate to lock the two members 12, 14 together. In some embodiments, when the protrusion 42 and the peripheral extension 22 pass one another an audible "click" is provided. Thus, the protrusion 42 and the peripheral extension 22 may be employed as means for indicating that a secure connection between the members 12, 14 has been made. The secure connection is a function of both the interaction of the protrusion 42 and peripheral extension 22, as well as the pressure applied by the male inner wall portion 26 of the male member 12 to the gas-odor seal 52 of the female member 14. In some embodiments, the interior protrusion 42 is spaced apart from the upper wall 56 such that the peripheral extension 22 can slide between protrusion 42 and the upper wall 56. Thus, in some such embodiments, the male member 12 may be interlocked with and slidably coupled to the female member 14. In some embodiments, the gas-odor seal 52 wipes the inner wall portion 26 substantially clean as the female member 14 joins the male member 12.

Figure 5:
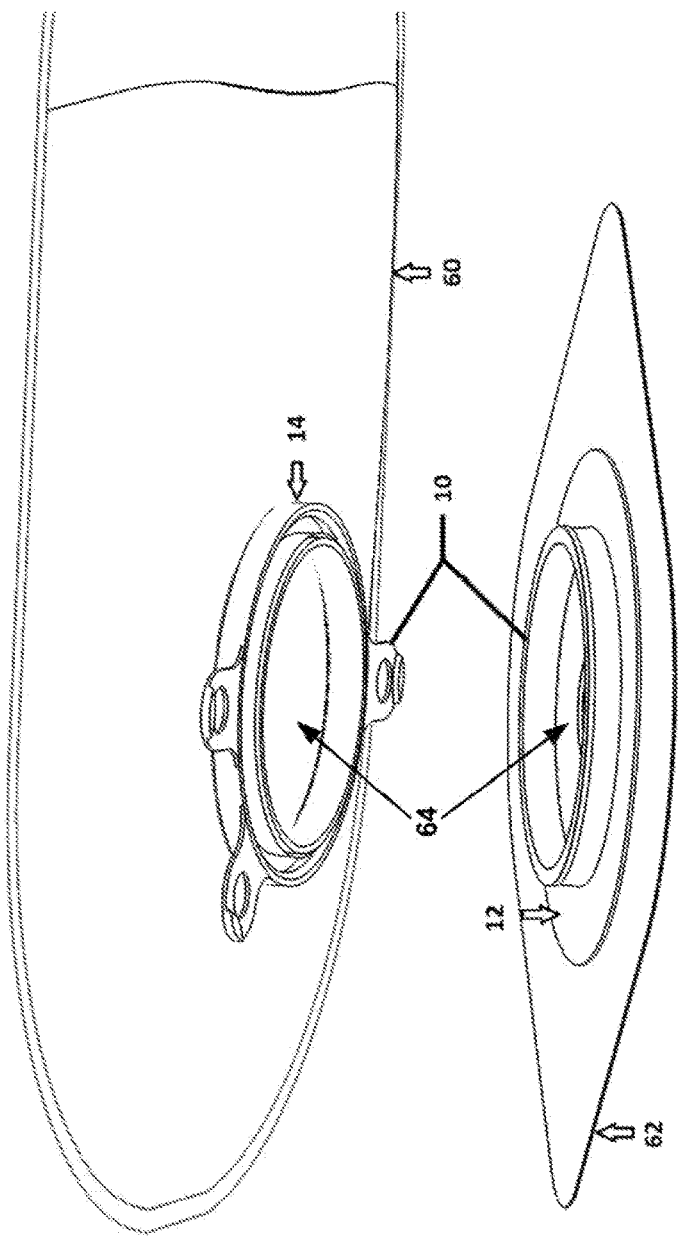
FIG. 5 is an isometric view of a coupling system within an ostomy pouch system.

FIG. 5 is an isometric view of a pouch 60 connected to the female member 14. Once the coupling system 10 is closed, i.e., the members 12, 14 are connected, the interior annular sidewall 46 of the female member 14 provides a clean surface for fecal matter transfer to the pouch 60. For example, with reference to FIG. 5, the female member 14 is shown connected to the pouch 60 and the male member 12 is shown connected to a tape collar 62 for coupling to a human body adjacent a wound site. Once the coupling system 10 is closed, the areas that can become impacted with fecal matter are minimized. In fact, the interior annular sidewall 46 of the female member 14 extends the length of the connected system 10, i.e., between lower and upper ends 48, 50 (see FIG. 3) of the female member 14 itself, to provide a flat interior surface to allow fecal matter to pass through a center aperture or passageway 64 of the coupling system 10 unobstructed (see FIG. 5).

Additionally, upon closure of the coupling system 10, the interaction of the male member 12 and the female member 14, as noted above, cooperate through the sliding action of the gas-odor seal 52 and the inner wall portion 26 and maintain sealing integrity during normal body movements of the patient via the secure connection provided by the protrusion 42 and the peripheral extension 22. Such sliding action is effected through the provision of recesses 28, 54 in the members 12, 14, respectively. Further, the interior annular sidewall 46 of the female member 14 and the gas-odor seal 52 preferably taper outwardly, i.e., away from an axis Y (see FIG. 3) of the system 10, to provide consistent tension during normal body movements. Further, the protrusion 42 acts as a security feature to maintain the sealing integrity of the system 10 when engaged with the peripheral extension 22.

The apparatuses, methods, and systems disclosed herein provide consistent pressure, while maintaining security through the interaction of several components in concert. As patients utilize the coupling system 10, the pouch side containing the female member 14 may be replaced in a three to one ratio with respect to the male member 12. As the user removes the pouch 60, the fecal matter is transferred to the pouch with substantially no retention of fecal matter within the body side coupling of the male member 12. Thus, the embodiments disclosed herein provide a more hygienic, flexible, and resilient coupling system than traditional coupling systems.

Numerous modifications to the embodiments disclosed herein will be apparent to those skilled in the art in view of the foregoing description. For example, any of the embodiments disclosed herein may be modified to include any of the structures or/or methodologies disclosed in connection with different embodiments. Accordingly, this disclosure is to be construed as illustrative only and is presented for the purpose of enabling those skilled in the art to make and use the invention and to teach the best mode of carrying out same. The exclusive rights to all modifications which come within the scope of the appended claims are reserved.

I claim:

1. An apparatus, comprising:
   a male coupling including a first sidewall having a first wall portion, a second wall portion, and a first recess between the first wall portion and the second wall portion, the first recess enabling relative movement between the first wall portion and the second wall portion; and
   a female coupling to be coupled to a pouch, the female coupling including a second sidewall and an interior wall spaced apart from the second sidewall, the interior wall having a flexible member, wherein the flexible member and the interior wall of the female coupling provide a second recess that is smaller than the first recess,
   wherein the first sidewall of the male coupling is configured to be received between the second sidewall and the interior wall of the female coupling to form a seal between the second wall portion of the male coupling and the flexible member of the female coupling, and
   wherein a thickness of the flexible member is smaller than a thickness of the interior wall.

2. The apparatus of claim 1, wherein the male coupling includes a peripheral extension.

3. The apparatus of claim 2, wherein the female coupling includes a protrusion configured to cooperate with the peripheral extension to lock the female coupling to the male coupling.

4. The apparatus of claim 1, wherein the first recess extends from a first end of the first sidewall to a medial portion of the first sidewall.

5. The apparatus of claim 1, wherein the female coupling is slidably coupled to the male coupling when the first sidewall of the male coupling is received between the second sidewall and the interior wall of the female coupling.

6. The apparatus of claim 1, wherein the first recess is annular.

7. The apparatus of claim 1, wherein the first wall portion has a first lower end extending to a first plane, and the second wall portion has a second lower end extending to a second plane parallel to and spaced apart from the first plane.

8. The apparatus of claim 7, wherein the second lower end extends past a medial portion of the first wall portion.

9. An apparatus, comprising:
   a first coupling including a sidewall having an annular spring and an extension; and
   a second coupling to be coupled to the first coupling, the second coupling having a protrusion and an annular wall including a seal, wherein the seal engages the annular spring and the extension is movable relative to the second coupling when the second coupling is coupled to the first coupling,
   wherein a thickness of the annular wall and a thickness of the seal are different.

10. The apparatus of claim 9, wherein the annular spring comprises a first wall portion and a second wall portion defining a recess between the first wall portion and the second wall portion.

11. The apparatus of claim 10, wherein the first wall portion has a first lower end extending to a first plane, and the second wall portion has a second lower end extending to a second plane parallel to and spaced apart from the first plane.

12. The apparatus of claim 9, wherein the sidewall of the first coupling is a first sidewall, and wherein a portion of the first sidewall is configured to be received in a channel between the annular wall and a second sidewall of the second coupling.

13. The apparatus of claim 12, wherein a medial wall extends between the annular wall and the second sidewall of the second coupling.

14. The apparatus of claim 9 further comprising a tape collar coupled to the first coupling.

15. The apparatus of claim 9, wherein the first coupling and the second coupling define a passageway.

16. The apparatus of claim 9, wherein the extension and the protrusion are configured to lockingly engage the first coupling and the second coupling.

17. An apparatus, comprising:
   a male coupling including a first sidewall having a generally V-shaped cross-sectional profile and a first recess; and
   a female coupling including a second sidewall having a generally U-shaped cross-sectional profile and a seal providing a second recess, the first sidewall configured to interlock with the second sidewall,
   wherein the second sidewall is thicker than the seal, and
   wherein the second recess is smaller than the first recess.

18. The apparatus of claim 17, wherein the first sidewall includes an outwardly extending extension and the second sidewall includes an inwardly extending protrusion, the extension and the protrusion configured to interlock the male coupling with the female coupling.

19. The apparatus of claim 17, wherein the first sidewall defines a first aperture and the second sidewall defines a second aperture, the first aperture and the second aperture configured to define a passageway when the male coupling is interlocked with the female coupling.

20. The apparatus of claim 17, wherein the second recess is defined between the seal and a portion of the second sidewall.

* * * * *